United States Patent [19]
Tateba et al.

[11] Patent Number: 5,227,007
[45] Date of Patent: Jul. 13, 1993

[54] PROCESS FOR PRODUCING CRYSTALS OF SALT OF ACIDIC AMINO ACID AND BASIC AMINO ACID

[75] Inventors: Tadao Tateba; Michio Shiomi, both of Hofu, Japan

[73] Assignee: Kyowa Hakko Kogyo Co., Ltd., Tokyo, Japan

[21] Appl. No.: 767,904

[22] Filed: Sep. 30, 1991

[30] Foreign Application Priority Data

Sep. 28, 1990 [JP] Japan .................. 2-259383

[51] Int. Cl.$^5$ .............................. C30B 7/06
[52] U.S. Cl. ................... 156/621; 156/600; 156/DIG. 90; 156/DIG. 113; 562/562; 564/477
[58] Field of Search ........... 156/600, 621, DIG. 113, 156/DIG. 90; 562/562; 564/477

[56] References Cited

U.S. PATENT DOCUMENTS

| | | | |
|---|---|---|---|
| 3,360,549 | 12/1967 | Marumo et al. | 260/501.11 |
| 3,952,060 | 4/1976 | Huber-Emden et al. | 564/477 |
| 4,052,372 | 10/1977 | Finet et al. | 530/333 |
| 4,420,432 | 12/1983 | Chibata et al. | 562/562 |
| 4,608,373 | 8/1986 | Shibanuma et al. | 540/227 |
| 5,089,492 | 2/1992 | Gerling et al. | 562/562 |

FOREIGN PATENT DOCUMENTS 965647 8/1964 United Kingdom .
1607742 5/1967 United Kingdom .

*Primary Examiner*—Robert Kunemund
*Attorney, Agent, or Firm*—Antonelli, Terry, Stout & Kraus

[57] ABSTRACT

Disclosed is a process for producing crystals of a salt of an acidic amino acid and a basic amino acid, which comprises adding a water-miscible solvent to an aqueous solution of the salt to prepare a solution 90% or more saturated or supersaturated with the salt, heating the resultant solution under reflux until the formation of crystals stops, adding gradually a water-miscible solvent to the solution under reflux to form crystals of the salt, and recovering the crystals from the resultant mixture.

12 Claims, 2 Drawing Sheets

PROCESS FOR PRODUCING CRYSTALS OF SALT OF ACIDIC AMINO ACID AND BASIC AMINO ACID

BACKGROUND OF THE INVENTION

The present invention relates to a process for producing crystals of salts of acidic amino acids and basic amino acids such as ornithine aspartate (referred to as OR.AS hereinafter), arginine aspartate (referred to as AR.AS hereinafter), and lysine glutamate (referred to as LY.GL hereinafter).

An equimolar mixture of an acidic amino acid and a basic amino acid has a high water solubility and thus crystals of a salt of an acidic amino acid and a basic amino acid cannot be obtained by the crystallization by concentration usually used for amino acids. In order to obtain crystals of such salts, a process in which methanol or the like is added to an aqueous solution of the salt to lower the solubility (normal crystallization procedure), a process in which an aqueous solution of the salt is added dropwise to a large amount of a solvent (reverse crystallization procedure), etc. have been so far employed.

In the normal crystallization procedure, precipitated particles tend to aggregate with one another owing to the low crystallinity of a salt of an acidic amino acid and a basic amino acid, and sometimes form a sticky mass to cause a failure in the separation of crystals. Therefore, the reverse crystallization procedure is generally employed. However, the product obtained by this procedure contain amorphous solid and it is pointed out that the resulting product has problems in quality such as contamination with other amino acids and the ash contained as impurities in the amino acids used as raw materials and the inequality in molarity of the two amino acids which form a salt. Further, there are also problems such as difficulty in the removal of a solvent in the drying step.

SUMMARY OF THE INVENTION

According to the present invention, crystals of a salt of an acidic amino acid and a basic amino acid (hereinafter referred to as amino acid salt) can be produced by adding a water-miscible solvent to an aqueous solution of the amino acid salt to prepare a solution 90% or more saturated or supersaturated with the salt, heating the resultant solution under reflux until the formation of crystals stops, adding gradually a water-miscible solvent to the solution under reflux to form crystals of the salt, and recovering the crystals of the salt from the resultant mixture.

DETAILED DESCRIPTION OF THE INVENTION

Figure 1:
FIGS. 1, 2, 3 and 4 show the structures of crystals of the amino acid salts obtained in Example 1, Comparative Example 1, Example 2 and Comparative Example 2, respectively.
Figure 2:
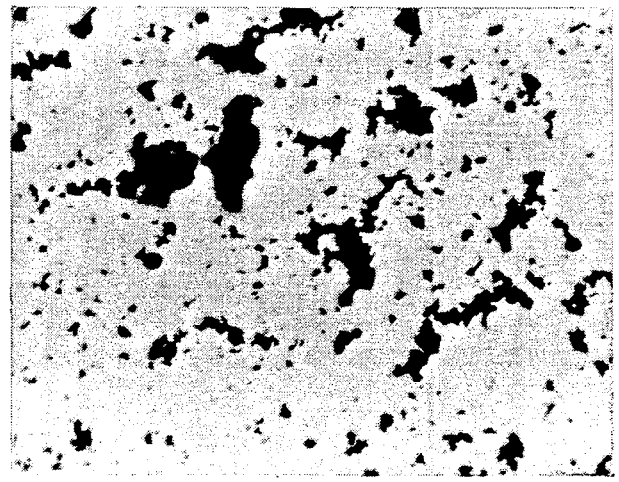
Figure 3:
Figure 4:
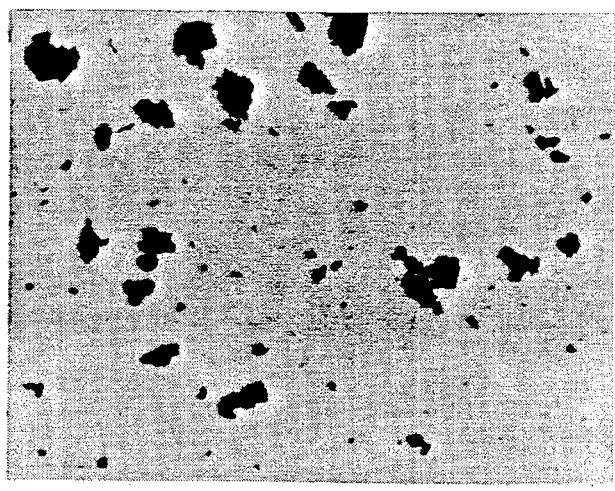

Examples of the acidic amino acids are aspartic acid and glutamic acid. Examples of the basic amino acids are ornithine, arginine and lysine.

The present invention can be carried out according to the following procedure.

(1) An aqueous solution of an amino acid salt is prepared by a known method, for example, by mixing an acidic amino acid and a basic amino acid in water.

Preferably, a salt solution prepared by dissolving equimolar amounts of an acidic amino acid and a basic amino acid in water is used.

The salt solution is used at a concentration of 0.5–2 molar concentration, preferably 1.3–1.7 molar concentration.

A water-miscible solvent such as methanol, ethanol or acetone is added to the aqueous solution of the amino acid salt to prepare a solution 90% or more saturated or preferably supersaturated with the salt.

(2) The resultant solution is heated to 70°–80° C. under reflux. Crystals of the amino acid salt start to deposit 1–30 minutes after the start of reflux.

The crystallization can start earlier by adding seed crystals to the solution prior to the reflux.

The heating under reflux is continued, whereby the solution turns turbid owing to the increase of deposit of crystals. The crystallization stops 30 minutes to 3 hours after the start of reflux. The stop of crystallization can be confirmed by the stop of the increase of turbidity.

(3) A water-miscible solvent, usually the same solvent as used in step (1), is gradually added to the resultant mixture under reflux to crystallize the amino acid salt still dissolved in the mixture and to enhance the crystallinity. The solvent is added at such a slow rate that amorphous deposit is not formed. The appropriate addition rate can be readily determined by an experiment.

The crystals further deposit by the addition of the solvent, and the crystallinity increases. When the crystallinity reaches an equilibrium, that is, when the formation of crystals substantially stops, the addition of the solvent is stopped.

The equilibrium point of crystallinity can be easily determined by an experiment in advance.

(4) After the addition of the solvent is completed and the absence of amorphous product in the resulting slurry is confirmed, the slurry is cooled to 20°–30° C. In cases where the amorphous product is present, the heating under reflux is further continued until the crystallization is completed.

(5) Crystals are separated from the cooled slurry by centrifugation or filtration and dried in vacuo or with hot air to obtain a product.

Certain embodiments of the invention are illustrated in the following examples.

Example 1 Production of OR.AS

Two hundred grams of crude crystals of ornithine (hydrochloride) was dissolved in 2l of water, and the solution was passed through a column of 2l of Diaion SK1B (Mitsubishi Kasei Corporation) to adsorb ornithine thereon. Elution was carried out with 2l of 2N NH$_4$OH, and 2.5l of the resulting solution of ornithine in aqueous ammonia was concentrated under reduced pressure to obtain 0.5l of an aqueous solution of ornithine at a concentration of 314 g/l with a percent ornithine recovery of 98%. To this solution was added 130 g of aspartic acid to prepare an OR.AS solution containing ornithine and aspartic acid in a molar ratio of 1:1 at pH 6.4. Then, 560 ml of the solution was heated to 50° C., and 340 ml of methanol was added thereto. No crystal precipitation was observed at that time. If 20 ml of methano are further added, amorphous precipitates were formed. The saturated OR.AS solution in aqueous methanol was heated to 75° C. and refluxed. The solution turned turbid after about 30 minutes and the turbidity reached an equilibrium 3 hours after the start of reflux. By inspecting the turbidity with a microscope, it was found that it consisted of columnar crystals and did not contain amorphous solid.

Then, 1.2l of methanol was added to the solution over one hour under reflux, followed by reflux for further 2 hours. The solution was then cooled to 25° C., and crystals were separated from the resulting slurry and dried in a vacuum drier to obtain 267 g of a product. The pH of a solution containing 10 g of the product in 100 ml of water was 6.4, which was the same as that of the equimolar composition.

Comparative Example 1 Production of OR.AS by the reverse crystallization procedure An aqueous solution of ornithine (0.5l) at a concentration of 314 g/l was prepared in the same manner as in Example 1. To the solution was added 124 g of crystals of aspartic acid to prepare an OR.AS solution containing ornithine and aspartic acid in a molar ratio of 1.05:1.00 at pH 7.3.

Then, 560 ml of the OR.AS solution was added dropwise to 4l of methanol heated to 50° C. at a rate of 100 ml/hr. In order to increase the crystallinity of precipitates after the dropping, the temperature of the slurry was raised to 70° C., followed by reflux. The formed precipitates partially showed polarization of light, but the precipitates did not completely turn to crystals showing polarization of light even by prolonging the reflux time. Then, the slurry was cooled to 25° C., and crystals were separated from the slurry and dried in a vacuum drier to obtain 258 g of a product. The pH of a solution containing 10 g of the product in 100 ml of water was 5.7, which was lower than pH 6.4 in the case of equimolar composition. In spite of a higher ornithine content in the initially prepared solution for crystallization, the aspartic acid content was higher in the product.

The results of analysis of the products obtained in the foregoing Example 1 and Comparative Example 1 are shown in Table 1.

TABLE 1

|  | Example 1 | Comparative Example 1 |
| --- | --- | --- |
| pH (100 g/l) | 6.4 | 5.7 |
| Lysine content* | 0.05% | 0.2% |
| Ignition residue | 0.01% | 0.05% |
| Aspartic acid/ornithine ratio | 0.999 | 1.026 |
| Methanol content | 0.007% | 0.08% |
| Crystallinity | 82% | 75% |

*Resulting from 0.4% lysine hydrochloride contained in the crude crystals of ornithine used.

Example 2 Production of AR.AS

Crystals of arginine (174 g) and 133 g of crystals of aspartic acid were dissolved in water to prepare 550 ml of an AR.AS solution. Then, 550 ml of the AR.AS solution was heated to 50° C., and 400 ml of methanol was added thereto. No precipitates were found at that time. After 1 g of seed crystals of AR.AS was added to the solution, the solution was heated to 75° C. and refluxed. The solution turned turbid immediately, and the turbidity reached an equilibrium after 30 minutes. Inspection of the turbidity with a microscope revealed that the turbidity consisted of columnar crystals. Then, 1.2l of methanol was added to the solution over one hour under reflux, followed by cooling to 25° C. All the particles in the resulting slurry were found to be columnar crystals. The crystallinity was 86%.

Comparative Example 2 Production of AR.AS by the normal crystallization procedure An AR.AS solution (550 ml) was prepared in the same manner as in Example 2. The solution was heated to 50° C., and 1.5l of methanol was added thereto over 5 hours. After the completion of the addition, the resulting slurry was inspected with a microscope. The slurry contained some crystals showing polarization of light, but most of the deposit was found to be amorphous. The slurry was then heated to 70° C. and refluxed for 3 hours. The final crystallinity obtained was 79% and the improvement in crystallinity was only slight.

What is claimed is:

1. A process for producing crystals of a salt of an acidic amino acid and a basic amino acid, which comprises adding a water-miscible solvent to an aqueous solution of the salt to prepare a solution of 90% or more saturated or supersaturated with the salt, heating the resultant solution to 70°-80° C. under reflux for 30 minutes to 3 hours until the formation of crystals stops, adding gradually a water-miscible solvent to the solution under reflux to form crystals of the slat, and recovering the crystals of the salt form the resultant mixture.

2. The process according to claim 1, wherein said acidic amino acid is aspartic acid.

3. The process according to claim 1, wherein said basic amino acid is a member selected from ornithine and arginine.

4. The process according to claim 1, wherein said salt is a member selected from ornithine aspartate and arginine aspartate.

5. The process according to claim 1, wherein said salt solution is one prepared by mixing equimolar amounts of the acidic amino acid and the basic amino acid.

6. The process according to claim 1, wherein the concentration of the salt solution is 0.5-2.0 molar concentration.

7. The process according to claim 1, wherein the water-miscible solvent is added to the amino acid salt solution to prepare a supersaturated solution.

8. A process for producing crystals of a salt of an acidic amino acid and a basic amino acid, which comprises adding a water-miscible solvent to an aqueous solution of the slat to prepare a solution 90% or more saturated or supersaturated with the salt, heating the resultant solution under reflux until the formation of crystals stops, adding gradually a water-miscible solvent to the solution under reflux to form crystals of the salt, and recovering the crystals of the salt from the resultant mixture.

9. The process according to any one of claims 1 to 8, wherein said water-miscible solvent is a member selected from methanol, ethanol and acetone.

10. A process according to claim 1, wherein the water-miscible solvent is gradually added to the reflux at such a slow rate that amorphous deposit is not formed.

11. A process according to claim 1, wherein the water-miscible solvent gradually added to the solution under reflux is the same water-miscible solvent added to the aqueous solution of the salt.

12. A process for producing crystals of ornithine aspartate, which comprises adding methanol to an aqueous solution of ornithine aspartate to prepare a supersaturated solution, heating the resultant solution under reflux until the formation of crystals stops, adding gradually methanol to the solution under reflux to form crystals of ornithine aspartate, and recovering the crystals from the resultant mixture.

* * * * *